ID
US009593107B2

United States Patent
Aebi et al.

(10) Patent No.: US 9,593,107 B2
(45) Date of Patent: *Mar. 14, 2017

(54) DIHYDROQUINOLINE-2-ONE DERIVATIVES

(71) Applicant: Hoffmann-La Roche Inc., Little Falls, NJ (US)

(72) Inventors: Johannes Aebi, Binningen (CH); Kurt Amrein, Itingen (CH); Benoit Hornsperger, Altkirch (FR); Bernd Kuhn, Reinbach BL (CH); Hans P. Maerki, Basel (CH); Alexander V. Mayweg, Basel (CH); Xuefei Tan, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/850,052

(22) Filed: Sep. 10, 2015

(65) Prior Publication Data

US 2015/0376180 A1 Dec. 31, 2015

Related U.S. Application Data

(63) Continuation of application No. PCT/EP2014/054642, filed on Mar. 11, 2014.

(51) Int. Cl.
*C07D 417/14* (2006.01)
*C07D 401/14* (2006.01)

(52) U.S. Cl.
CPC .......... *C07D 417/14* (2013.01); *C07D 401/14* (2013.01)

(58) Field of Classification Search
CPC .................. C07D 417/14; C07D 401/14
See application file for complete search history.

(56) References Cited

U.S. PATENT DOCUMENTS 9,260,408 B2 * 2/2016 Aebi .................. C07D 401/04

FOREIGN PATENT DOCUMENTS

| CN | 105102445 A | 11/2015 |
|---|---|---|
| WO | 2009/135651 A1 | 11/2009 |
| WO | 2013/037779 A1 | 3/2013 |
| WO | 2015/135561 A1 | 9/2014 |

OTHER PUBLICATIONS

ISR for PCT/EP2014/054642.
Written Opinion for PCT/EP2014/054642.

* cited by examiner

*Primary Examiner* — D M Seaman
(74) *Attorney, Agent, or Firm* — Robert C. Hall

(57) ABSTRACT

The invention provides novel compounds having the general formula (I)

(I)

wherein $R^1$, $R^2$, $R^3$, $R^4$, $R^5$, $R^6$, $R^7$, $R^9$, $R^{10}$ and $R^{11}$ are as described herein, compositions including the compounds and methods of using the compounds.

22 Claims, No Drawings

DIHYDROQUINOLINE-2-ONE DERIVATIVES

The present invention relates to organic compounds useful for therapy or prophylaxis in a mammal, and in particular to aldosterone synthase (CYP11B2 or CYP11B1) inhibitors for the treatment or prophylaxis of chronic kidney disease, congestive heart failure, hypertension, primary aldosteronism and Cushing syndrome.

The present invention provides novel compounds of formula (I)

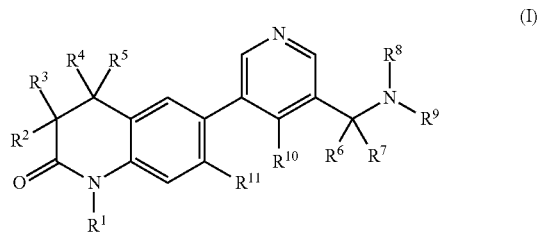

wherein
$R^1$ is H, alkyl, haloalkyl, cycloalkyl or halocycloalkyl;
$R^2$ is H, alkyl, haloalkyl, cycloalkyl or halocycloalkyl;
$R^3$ is H, alkyl, haloalkyl, cycloalkyl or halocycloalkyl;
$R^4$ is H, alkyl, haloalkyl, cycloalkyl or halocycloalkyl;
or $R^3$ and $R^4$ together with the carbon atoms to which they are attached form a double bond;
$R^5$ is H, alkyl, haloalkyl, cycloalkyl or halocycloalkyl;
$R^6$ is H, alkyl, haloalkyl, cycloalkyl or halocycloalkyl;
$R^7$ is H, alkyl, haloalkyl, cycloalkyl or halocycloalkyl;
or $R^6$ and $R^7$ together with the carbon atom to which they are attached form a cycloalkyl;
$R^8$ and $R^9$ together with the nitrogen atom to which they are attached form a heteroaryl substituted with an oxo substituent and one to three substitutents independently selected from H, halogen, cyano, alkyl, haloalkyl, cycloalkyl and halocycloalkyl;
$R^{10}$ is H, halogen, alkyl, haloalkyl, cycloalkyl or halocycloalkyl;
$R^{11}$ is H, halogen, alkyl, haloalkyl, cycloalkyl or halocycloalkyl;
or pharmaceutically acceptable salts or esters.

Herein we describe inhibitors of aldosterone synthase that have the potential to protect from organ/tissue damage caused by an absolute or relative excess of aldosterone. Hypertension affects about 20% of the adult population in developed countries. In persons 60 years and older, this percentage increases to above 60%. Hypertensive subjects display an increased risk of other physiological complications including stroke, myocardial infarction, atrial fibrillation, heart failure, peripheral vascular disease and renal impairment. The renin angiotensin aldosterone system is a pathway that has been linked to hypertension, volume and salt balance and more recently to contribute directly to end organ damage in advanced stages of heart failure or kidney disease. ACE inhibitors and angiotensin receptor blockers (ARBs) are successfully used to improve duration and quality of life of patients. These drugs are not yielding maximum protection. In a relatively large number of patients ACE and ARB's lead to so-called aldosterone breakthrough, a phenomenon where aldosterone levels, after a first initial decline, return to pathological levels. It has been demonstrated that the deleterious consequences of inappropriately increased aldosterone levels (in relation to salt intake/levels) can be minimized by aldosterone blockade with mineralocorticoid receptor antagonists. A direct inhibition of aldosterone synthesis is expected to provide even better protection as it will also reduce non-genomic effects of aldosterone as well.

The effects of aldosterone on Na/K transport lead to increased re-absorption of sodium and water and the secretion of potassium in the kidneys. Overall this results in increased blood volume and, therefore, increased blood pressure. Beyond its role in the regulation of renal sodium re-absorption aldosterone can exert deleterious effects on the kidney, the heart and the vascular system especially in a "high sodium" context. It has been shown that under such conditions aldosterone leads to increased oxidative stress which ultimately may contribute to organ damage. Infusion of aldosterone into renally compromised rats (either by high salt treatment or by unilaterally nephrectomy) induces a wide array of injuries to the kidney including glomerular expansion, podocyte injury, interstitial inflammation, mesangial cell proliferation and fibrosis reflected by proteinuria. More specifically aldosterone was shown to increase the expression of the adhesion molecule ICAM-1 in the kidney. ICAM-1 is critically involved in glomerular inflammation. Similarly, aldosterone was shown to increase the expression of inflammatory cytokines, such as interleukin IL-1b and IL-6, MCP-1 and osteopontin. On a cellular level it was demonstrated that in vascular fibroblasts aldosterone increased the expression of type I collagen mRNA, a mediator of fibrosis. Aldosterone also stimulates type IV collagen accumulation in rat mesangial cells and induces plasminogen activator inhibitor-1 (PAI-1) expression in smooth muscle cells. In summary aldosterone has emerged as a key hormone involved in renal damage. Aldosterone plays an equally important role in mediating cardiovascular risk.

There is ample preclinical evidence that MR-antagonists (spironolactone and eplerenone) improve blood pressure, cardiac and renal function in various pre-clinical models.

More recently preclinical studies highlight the important contribution of CYP11B2 to cardiovascular and renal morbidity and mortality. The CYP11B2 inhibitor FAD286 and the MR antagonist spironolactone were evaluated in a rat model of chronic kidney disease (high angiotensin II exposure; high salt and uni-nephrectomy). Angiotensin II and high salt treatment caused albuminuria, azotemia, renovascular hypertrophy, glomerular injury, increased PAI-1, and osteopontin mRNA expression, as well as tubulointerstitial fibrosis. Both drugs prevented these renal effects and attenuated cardiac and aortic medial hypertrophy. Following 4 weeks of treatment with FAD286, plasma aldosterone was reduced, whereas spironolactone increased aldosterone at 4 and 8 weeks of treatment. Similarly only spironolactone but not FAD286 enhanced angiotensin II and salt-stimulated PAI-1 mRNA expression in the aorta and the heart. In other studies the CYP11B2 inhibitor FAD286 improved blood pressure and cardiovascular function and structure in rats with experimental heart failure. In the same studies FAD286 was shown to improve kidney function and morphology.

Administration of an orally active CYP11B2 inhibitor, LCI699, to patients with primary aldosteronism, lead to the conclusion that it effectively inhibits CYP11B2 in patients with primary aldosteronism resulting in significantly lower circulating aldosterone levels and that it corrected the hypokalemia and mildly decreased blood pressure. The effects on the glucocorticoid axis were consistent with a poor selectivity of the compound and a latent inhibition of cortisol synthesis. Taken together these data support the concept that a CYP11B2 inhibitor can lower inappropriately high aldosterone levels. Achieving good selectivity against CYP11B1 is important to be free of undesired side effects on the HPA axis and will differentiate different CYP11B2 inhibitors.

The compounds of the present invention according formula (I) are potent inhibitors of CYP11B2 and present an improved selectivity towards CYP11B2 versus CYP11B1.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of chronic kidney disease, congestive heart failure, hypertension, primary aldosteronism and Cushing syndrome and the use of the said compounds, salts or esters for the production of medicaments for the treatment or prophylaxis of chronic kidney disease, congestive heart failure, hypertension, primary aldosteronism and Cushing syndrome.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, and. Particular alkyl groups include methyl, ethyl, propyl and isopropyl. More particular alkyl group is methyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "cyano" denotes a —C≡N group.

The term "cycloalkyl" denotes a monovalent saturated monocyclic or bicyclic hydrocarbon group of 3 to 10 ring carbon atoms. In particular embodiments, cycloalkyl denotes a monovalent saturated monocyclic hydrocarbon group of 3 to 8 ring carbon atoms. Bicyclic means consisting of two saturated carbocycles having two carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl groups are cyclopropyl, cyclobutanyl, cyclopentyl and cyclohexyl. More articular monocyclic cycloalkyl group is cyclopropyl.

The term "haloalkyl" denotes an alkyl group wherein at least one of the hydrogen atoms of the alkyl group has been replaced by same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl groups are trifluoromethyl.

The term "halocycloalkyl" denotes a cycloalkyl group wherein at least one of the hydrogen atoms of the cycloalkyl group has been replaced by same or different halogen atoms, particularly fluoro atoms. Examples of halocycloalkyl groups include fluorocyclopropyl, difluorocyclopropyl, fluorocyclobutyl and difluorocyclobutyl.

The term "halogen" and "halo" are used interchangeably herein and denote fluoro, chloro, bromo, or iodo. Particular halogens are chloro and fluoro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl and quinoxalinyl. Particular heteroaryl groups include benzothiazolyl, thiatolyl, pyridinyl and pyrimidyl. Further particular heteroaryl group is pyridinyl.

Particular heteroaryl formed by $R^8$ and $R^9$ together with the nitrogen atom to which they are attached and substituted with an oxo group are groups A, B, C and D.

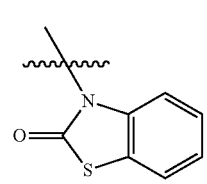

A

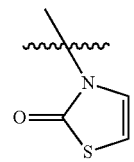

B

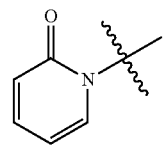

C

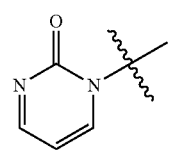

D

Further heteroaryl formed by $R^8$ and $R^9$ together with the nitrogen atom to which they are attached and substituted with an oxo group is group C.

The term "oxo" denotes a =O group.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc).

The abbreviation uM means microMolar and is equivalent to the symbol µM.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

Another embodiment of the present invention are compounds according to formula (I) as described herein, wherein $R^1$ is alkyl.

A further embodiment of the present invention are compounds according to formula (I) as described herein, wherein $R^2$ is H.

A particular embodiment of the present invention are compounds according to formula (I) as described herein, wherein $R^3$ is H.

In a further embodiment of the present invention are compounds according to formula (I) as described herein, wherein $R^4$ is H.

Another further embodiment of the present invention are compounds according to formula (I) as described herein, wherein $R^5$ is H.

Another embodiment of the present invention are compounds according to formula (I) as described herein, wherein $R^6$ is H.

The present invention also relates to compounds according to formula (I) as described herein, wherein $R^7$ is H.

A further particular embodiment of the present invention are compounds according to formula (I) as described herein, wherein $R^8$ and $R^9$ together with the nitrogen atom to which they are attached form a heteroaryl, substituted with an oxo substituent and one to three substitutents independently selected from H, halogen, cyano, alkyl and haloalkyl.

A more particular embodiment of the present invention are compounds according to formula (I) as described herein, wherein $R^8$ and $R^9$ together with the nitrogen atom to which they are attached form a substituted 2H-pyridinyl, a substituted pyrimidinyl, a substituted thiazolyl or a substituted benzothiazolyl, wherein substituted 2H-pyridinyl, substituted pyrimidinyl, substituted thiazolyl and substituted benzothiazolyl are substituted with an oxo substituent and one to three substitutents independently selected from H, halogen, cyano, alkyl and haloalkyl.

Also an embodiment of the present invention are compounds according to formula (I) as described herein, wherein $R^8$ and $R^9$ together with the nitrogen atom to which they are attached form oxo-2H-pyridinyl substituted one to three substitutents independently selected from H, halogen, cyano, alkyl and haloalkyl.

The present invention also relates to compounds according to formula (I) as described herein, wherein $R^8$ and $R^9$ together with the nitrogen atom to which they are attached form oxo-2H-pyridinyl substituted one to two substitutents independently selected from H, halogen and alkyl.

Another embodiment of the present invention are compounds according to formula (I) as described herein, wherein $R^8$ and $R^9$ together with the nitrogen atom to which they are attached form fluoro-oxo-2H-pyridinyl, chloro-oxo-2H-pyridinyl or methyl-oxo-2H-pyridinyl.

A particular embodiment of the present invention are compounds according to formula (I) as described herein, wherein $R^{10}$ is H or alkyl.

A particular embodiment of the present invention are compounds according to formula (I) as described herein, wherein $R^{10}$ is alkyl.

A particular embodiment of the present invention are compounds according to formula (I) as described herein, wherein $R^{11}$ is H or halogen.

Also an embodiment of the present invention are compounds according to formula (I) as described herein, wherein $R^{11}$ is halogen.

A particular embodiment of the present invention are compounds according to formula (I) as described herein, wherein the compounds are of formula (Ia) and $R^{12}$ and $R^{13}$ are independently selected from H, halogen and alkyl.

(Ia)

or pharmaceutically acceptable salts thereof.

Particular examples of compounds of formula (I) as described herein are selected from 1-Methyl-6-[5-(2-oxo-benzothiazol-3-ylmethyl)-pyridin-3-yl]-3,4-dihydro-1H-quinolin-2-one;
6-[5-(5-Fluoro-2-oxo-2H-pyridin-1-ylmethyl)-pyridin-3-yl]-1-methyl-3,4-dihydro-1H-quinolin-2-one;
1-Methyl-6-[5-(2-oxo-thiazol-3-ylmethyl)-pyridin-3-yl]-3,4-dihydro-1H-quinolin-2-one;
6-[5-(3-Chloro-2-oxo-2H-pyridin-1-ylmethyl)-pyridin-3-yl]-1-methyl-3,4-dihydro-1H-quinolin-2-one;
6-[5-(3-Fluoro-2-oxo-5-trifluoromethyl-2H-pyridin-1-ylmethyl)-pyridin-3-yl]-1-methyl-3,4-dihydro-1H-quinolin-2-one;
6-[5-(3-Fluoro-2-oxo-2H-pyridin-1-ylmethyl)-pyridin-3-yl]-1-methyl-3,4-dihydro-1H-quinolin-2-one;

1-Methyl-6-[5-(6-methyl-2-oxo-2H-pyridin-1-ylmethyl)-pyridin-3-yl]-3,4-dihydro-1H-quinolin-2-one;
1-Methyl-6-[5-(4-methyl-2-oxo-2H-pyridin-1-ylmethyl)-pyridin-3-yl]-3,4-dihydro-1H-quinolin-2-one;
6-[5-(5-Chloro-2-oxo-2H-pyridin-1-ylmethyl)-pyridin-3-yl]-1-methyl-3,4-dihydro-1H-quinolin-2-one;
1-Methyl-6-[5-(2-oxo-2H-pyridin-1-ylmethyl)-pyridin-3-yl]-3,4-dihydro-1H-quinolin-2-one;
1-Methyl-6-[5-(2-oxo-3-trifluoromethyl-2H-pyridin-1-ylmethyl)-pyridin-3-yl]-3,4-dihydro-1H-quinolin-2-one;
1-Methyl-6-[5-(2-methyl-6-oxo-6H-pyrimidin-1-ylmethyl)-pyridin-3-yl]-3,4-dihydro-1H-quinolin-2-one;
1-Methyl-6-[5-(2-oxo-2H-pyrimidin-1-ylmethyl)-pyridin-3-yl]-3,4-dihydro-1H-quinolin-2-one;
1-[5-(1-Methyl-2-oxo-1,2,3,4-tetrahydro-quinolin-6-yl)-pyridin-3-ylmethyl]-2-oxo-1,2-dihydro-pyridine-4-carbonitrile;
1-Methyl-6-[5-(2-oxo-5-trifluoromethyl-2H-pyridin-1-ylmethyl)-pyridin-3-yl]-3,4-dihydro-1H-quinolin-2-one;
1-[5-(1-Methyl-2-oxo-1,2,3,4-tetrahydro-quinolin-6-yl)-pyridin-3-ylmethyl]-6-oxo-1,6-dihydro-pyridine-3-carbonitrile;
6-[5-(6-Chloro-2-oxo-2H-pyridin-1-ylmethyl)-pyridin-3-yl]-1-methyl-3,4-dihydro-1H-quinolin-2-one;
6-[5-(6-Fluoro-2-oxo-2H-pyridin-1-ylmethyl)-pyridin-3-yl]-1-methyl-3,4-dihydro-1H-quinolin-2-one;
7-Fluoro-6-[5-(3-fluoro-2-oxo-2H-pyridin-1-ylmethyl)-pyridin-3-yl]-1-methyl-3,4-dihydro-1H-quinolin-2-one;
7-Fluoro-1-methyl-6-[5-(4-methyl-2-oxo-2H-pyridin-1-ylmethyl)-pyridin-3-yl]-3,4-dihydro-1H-quinolin-2-one;
6-[5-(5-Chloro-2-oxo-2H-pyridin-1-ylmethyl)-pyridin-3-yl]-7-fluoro-1-methyl-3,4-dihydro-1H-quinolin-2-one;
6-[5-(6-Chloro-2-oxo-2H-pyridin-1-ylmethyl)-pyridin-3-yl]-7-fluoro-1-methyl-3,4-dihydro-1H-quinolin-2-one;
7-Fluoro-1-methyl-6-[5-(6-methyl-2-oxo-2H-pyridin-1-ylmethyl)-pyridin-3-yl]-3,4-dihydro-1H-quinolin-2-one;
7-Fluoro-1-methyl-6-[4-methyl-5-(6-methyl-2-oxo-2H-pyridin-1-ylmethyl)-pyridin-3-yl]-3,4-dihydro-1H-quinolin-2-one;
6-[5-(6-Chloro-2-oxo-2H-pyridin-1-ylmethyl)-4-methyl-pyridin-3-yl]-7-fluoro-1-methyl-3,4-dihydro-1H-quinolin-2-one;
7-Fluoro-6-[5-(3-fluoro-2-oxo-2H-pyridin-1-ylmethyl)-4-methyl-pyridin-3-yl]-1-methyl-3,4-dihydro-1H-quinolin-2-one;
7-Fluoro-6-[5-(6-fluoro-2-oxo-2H-pyridin-1-ylmethyl)-4-methyl-pyridin-3-yl]-1-methyl-3,4-dihydro-1H-quinolin-2-one;
and pharmaceutically acceptable salts thereof.

Further particular examples of compounds of formula (I) as described herein are selected from
1-Methyl-6-[5-(2-oxo-benzothiazol-3-ylmethyl)-pyridin-3-yl]-3,4-dihydro-1H-quinolin-2-one;
6-[5-(3-Fluoro-2-oxo-2H-pyridin-1-ylmethyl)-pyridin-3-yl]-1-methyl-3,4-dihydro-1H-quinolin-2-one;
7-Fluoro-1-methyl-6-[5-(6-methyl-2-oxo-2H-pyridin-1-ylmethyl)-pyridin-3-yl]-3,4-dihydro-1H-quinolin-2-one;
7-Fluoro-1-methyl-6-[4-methyl-5-(6-methyl-2-oxo-2H-pyridin-1-ylmethyl)-pyridin-3-yl]-3,4-dihydro-1H-quinolin-2-one;
6-[5-(6-Chloro-2-oxo-2H-pyridin-1-ylmethyl)-4-methyl-pyridin-3-yl]-7-fluoro-1-methyl-3,4-dihydro-1H-quinolin-2-one;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein.

The following abbreviations are used in the present text:
AcOH=acetic acid, BOC=t-butyloxycarbonyl, BuLi=butyllithium, CDI=1,1-carbonyldiimidazole, $CH_2Cl_2$=dichloromethane, DBU=2,3,4,6,7,8,9,10-octahydro-pyrimido[1,2-a]azepine, DCE=1,2-dichloroethane, DIBALH=di-i-butylaluminium hydride, DCC=N,N'-dicyclohexylcarbodiimide, DMA=N,N-dimethylacetamide, DMAP=4-dimethylaminopyridine, DMF=N,N-dimethylformamide, EDCI=N-(3-dimethylaminopropyl)-N'-ethylcarbodiimide hydrochloride, EtOAc=ethylacetate, EtOH=ethanol, $Et_2O$=diethylether, $Et_3N$=triethylamine, eq=equivalents, HATU=O-(7-azabenzotriazol-1-yl)-1,1,3,3-tetramethyluronium hexafluorophosphate, HPLC=high performance liquid chromatography, HOBT=1-hydroxybenzo-triazole, Huenig's base=$iPr_2NEt$=N-ethyl diisopropylamine, IPC=in process control, LAH=lithium aluminium hydride, LDA=lithium diisopropylamide, HMDS=hexamethydisilazane, $LiBH_4$=lithium borohydride, MeOH=methanol, $NaBH_3CN$=sodium cyanoborohydride, $NaBH_4$=sodium borohydride, NaI=sodium iodide, Red-Al=sodium bis(2-methoxyethoxy)aluminium hydride, RT=room temperature, TBDMSCl=t-butyldimethylsilyl chloride, TFA=trifluoroacetic acid, THF=tetrahydrofuran, quant=quantitative.

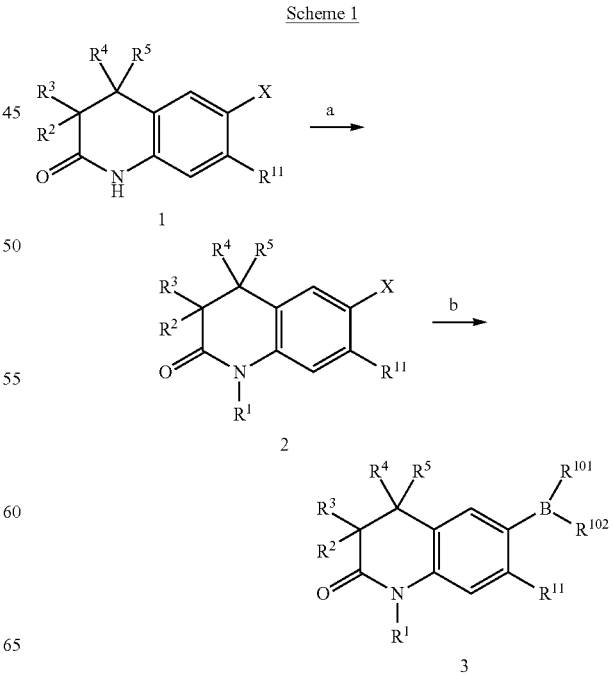

Scheme 1

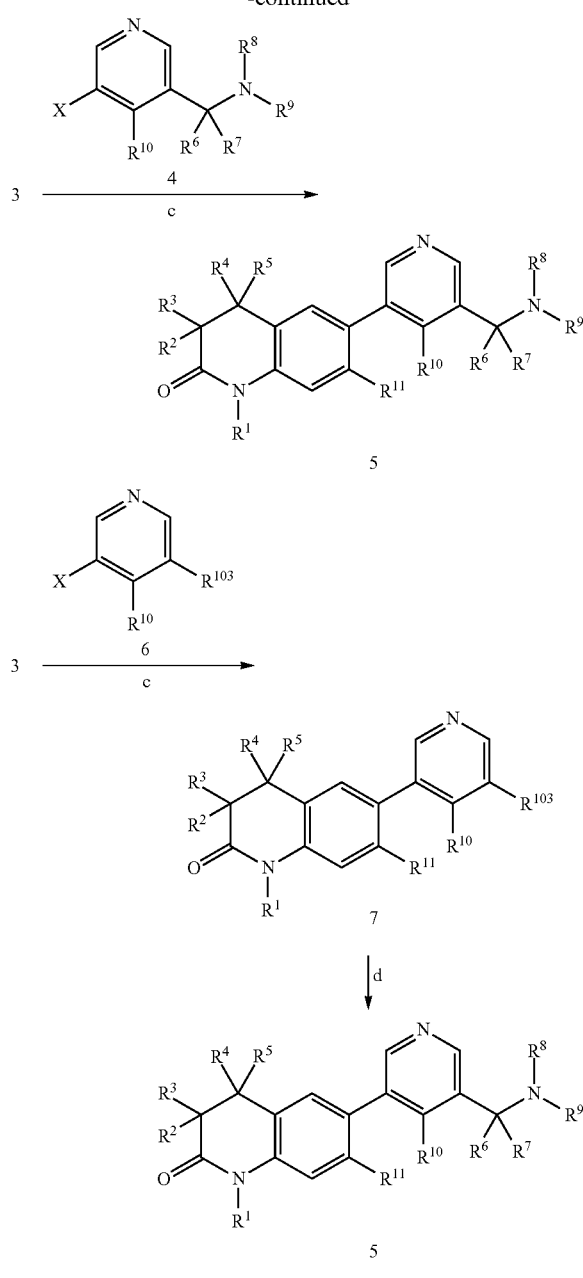

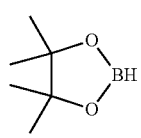

X is Halogen or OSO$_2$CF$_3$

R$^{101}$ and R$^{102}$ e.g. together with the boron atom to which they are attached form R$^{103}$ stands for substituents as e.g. shown in Schemes 2, 3, allowing at a later stage in the synthesis further transformation into

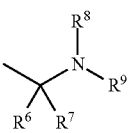

Lactam compounds 1 (Scheme 1) are known or can be prepared by methods described herein or known to the man skilled in the art. Compounds 1 can be alkylated at nitrogen using a base like sodium hydride or sodium or potassium tert-butoxide, followed by addition of an alkylating agent of formula R$^1$—Y, wherein Y is halogen, tosylate or mesylate, in a solvent like DMF or THF preferably in a temperature range between 0° C. and about 80° C. giving N-alkylated lactams 2 (step a).

Reaction of lactams 2 with e.g. 4,4,4',4',5,5,5',5'-octamethyl-2,2'-bi(1,3,2-5 dioxaborolane) in solvents like dimethylsulfoxide or dioxane in the presence of potassium acetate and catalysts like (1,1'-bis-diphenylphosphino)-ferrocene) palladium-(II)dichloride (1:1 complex with dichloromethane) at temperatures up to about 100° C. gives boronic ester compounds 3 (step b). Condensation of boronic ester compounds 3 with suitable aryl halides 4 or 6 (for possible syntheses of aryl halides 4 or 6, see Scheme 3) can be performed using Suzuki conditions, e.g. in the presence of catalysts, such as tri-o-tolylphosphine/palladium(II)acetate, tetrakis-(triphenylphosphine)-palladium, bis(triphenylphosphine)palladium(II)chloride or dichloro[1,1'-bis(diphenylphosphino)-ferrocene]palladium(II) optionally in the form of a dichloromethane complex (1:1), and in the presence of a base, such as aqueous or non-aqueous potassium phosphate, sodium or potassium carbonate, in a solvent, such as dimethylsulfoxide, toluene, ethanol, dioxane, tetrahydrofuran or N,N-dimethylformamide, and in an inert atmosphere such as argon or nitrogen, in a temperature range preferably between room temperature and about 130° C. leading to adducts 5 or 7 (steps c). Compounds 7 can be further transformed into compounds of the general formula 5 by methods described in the following Schemes, the examples or by methods well known to persons skilled in the art (step d).

Scheme 2

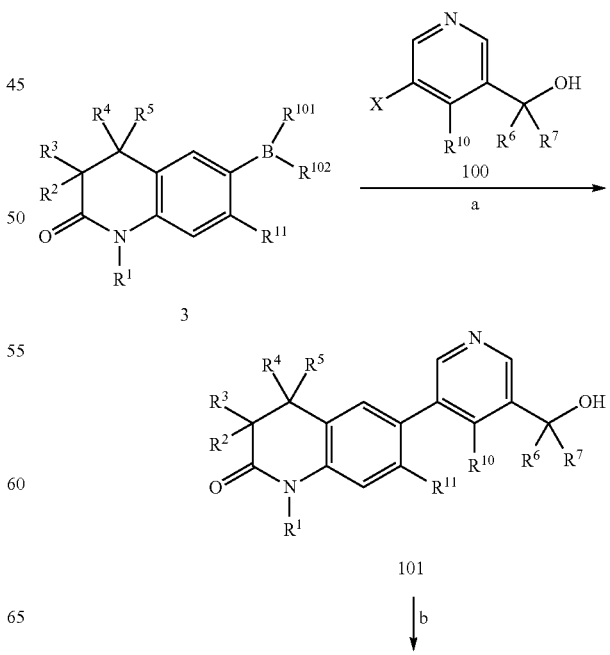

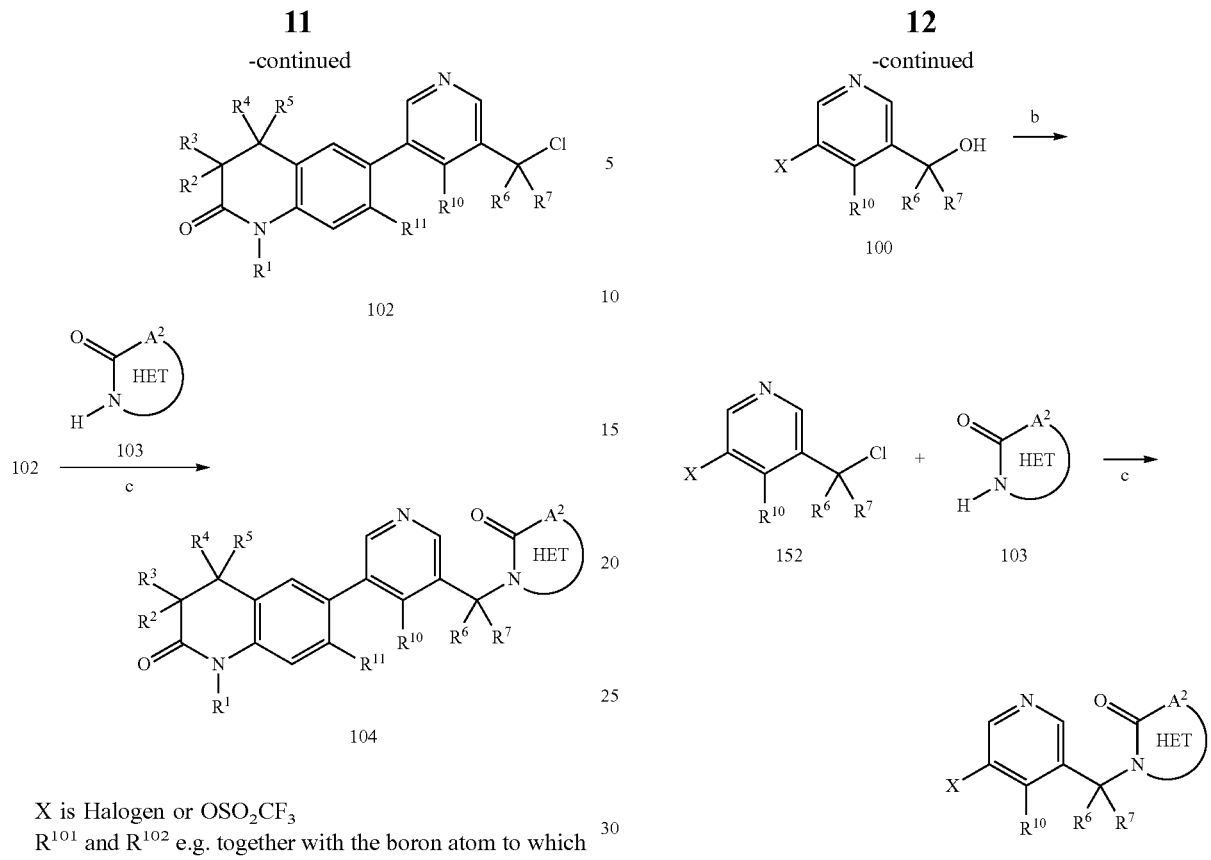

X is Halogen or OSO$_2$CF$_3$
R$^{101}$ and R$^{102}$ e.g. together with the boron atom to which they are attached form

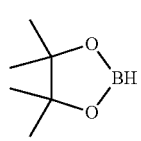

A$^2$ stands for an optionally substituted carbon or an optionally substituted heteroatom HET stands for heteroaryl as defined herein Suzuki reactions of hydroxy-alkyl substituted halo aryl compounds 100 (Scheme 2) with aryl-boronic acid derivatives 3 under conditions as described for step c (Scheme 1) followed by transformation of the OH into a chloro function e.g. by treatment with thionyl chloride in a solvent like DCM around room temperature give chloro alkyl compounds 102 (steps a, b). NH-Heteroaryles 103 react with chloroalkyl compounds 102 when treated with a base like cesium, sodium or potassium carbonate in solvents like DMF, acetonitrile or DMSO at temperatures between about 0° C. and the reflux temperature of the solvents to adducts 104 (step c).

Scheme 3

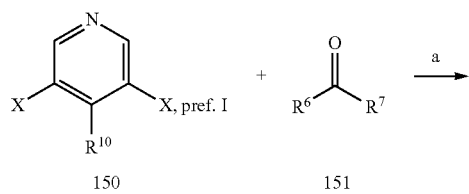

X is Halogen or OSO$_2$CF$_3$

A$^2$ stands for an optionally substituted carbon or an optionally substituted heteroatom HET stands for heteroaryl as defined herein Hydroxy-alkyl compounds 100 (Scheme 3) are known or can e.g. be prepared from di-halo pyridine compounds 150 and aldehydes or ketones 151 e.g. by treatment of the di-halo pyridine compounds 150 with nBuLi at −78° C., followed by reaction with aldehydes or ketones 151 in a solvent like THF again at a temperature around −78° C. and subsequent warming up to RT (step a).

Chloroalkyl compounds 152 can be obtained from hydroxy-alkyl compounds 100 by transformation of the OH into a chloro function e.g. by treatment with thionyl chloride in a solvent like DCM around room temperature (step b). NH-Heterocycles 103 react with chloroalkyl compounds 152 when treated with a base like cesium, sodium or potassium carbonate in solvents like DMF, acetonitrile or DMSO at temperatures between about 0° C. and the reflux temperature of the solvents to adducts 153 (step c). Optionally, compounds 153 with R$^6$ and/or R$^7$ different from hydrogen can be prepared by treatment of compounds 153 with R$^6$ and R$^7$ equal to hydrogen with a base like LDA or HMDS in solvents like tetrahydrofuran or 1,2-dimethoxyethane, followed by addition of a mono alkyl halide, an alpha, omega dihaloalkane or sequentially two different alkyl halides, reactions preferably performed between −78° C. and room temperature.

Halo aryl compounds 153 are examples of compounds 4 and suitable substrates for Suzuki reactions as described for step c (Scheme 1).

Scheme 4

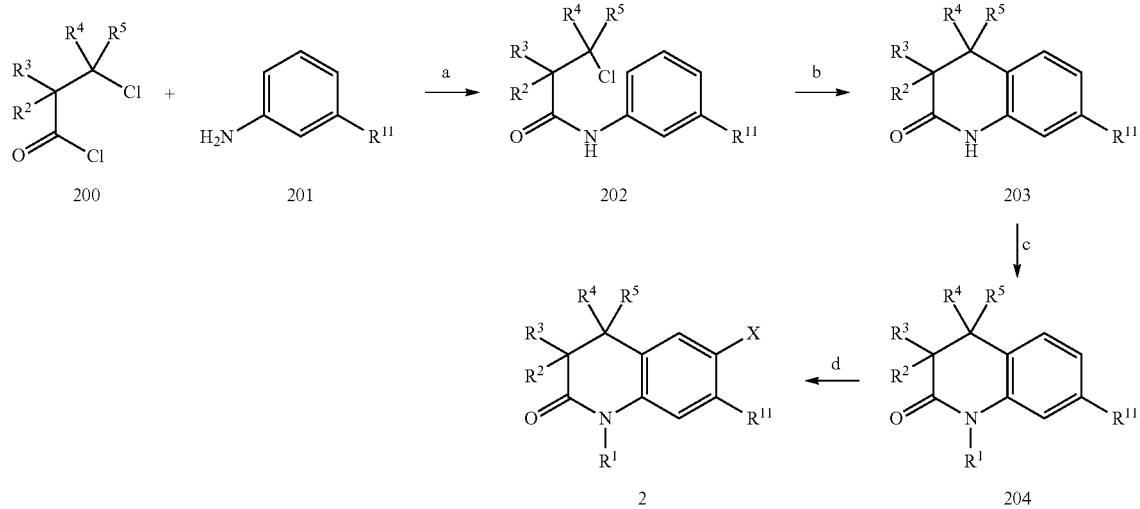

Chloropropionic acid anilides 202 (Scheme 4) can be prepared from chloro propionic acid chlorides 200 and anilines 201 by reaction in a solvent like DCM in the presence of a base like pyridine preferably around room temperature (step a). Chloropropionic acid anilides 202 undergo ring closure to lactam compounds 203 when treated with $AlCl_3$ preferably without solvent at elevated temperatures of e.g. 100 to 150° C. (step b). Lactam compounds 203 can be alkylated at nitrogen using a base like sodium hydride or sodium or potassium tert-butoxide, followed by addition of an alkylating agent of formula $R^1$—Y, wherein Y is halogen, tosylate or mesylate, in a solvent like DMF or THF preferably in a temperature range between 0° C. and about 80° C. giving N-alkylated lactams 204 (step c). Halogenation of N-alkylated lactams 204 can be performed e.g. by using N-bromo or N-chloro succinimide in solvents like DMF preferably around room temperature giving halo lactam compounds 2 with X equal to bromine or chlorine respectively (step d).

Also an embodiment of the present invention is a process to prepare a compound of formula (I) as defined above comprising the reaction of a compound of formula (II) in the presence of a compound of formula (III);

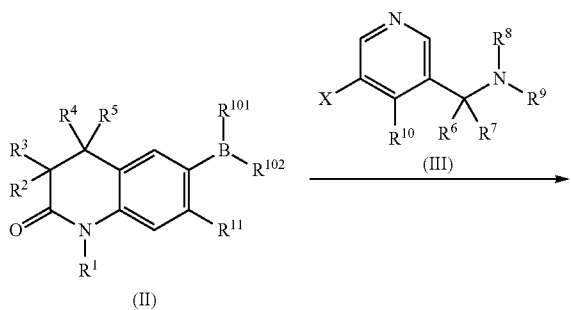

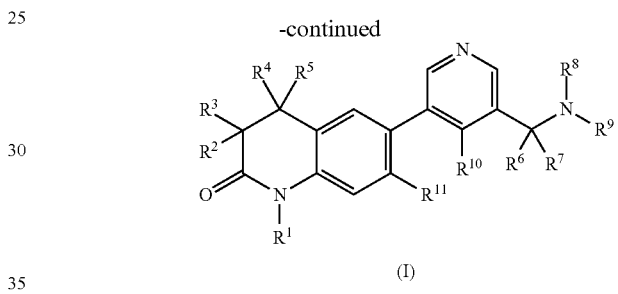

wherein $R^1$, $R^2$, $R^3$, $R^4$, $R^5$, $R^6$, $R^7$, $R^9$, $R^{10}$, $R^{11}$ and A are as defined above, $R^{101}$ and $R^{102}$ are independently selected from alkyl and cycloalkyl, or $R^{101}$ and $R^{102}$ together with the boron atom to which they are attached form a borolane and X is halogen or triflate.

In particular, in a solvent, such as dimethylsulfoxide, toluene, ethanol, dioxane, tetrahydrofuran or N,N-dimethylformamide, optionally with water, particularly ethanol or DMF, in the presence of catalysts, such as tri-o-tolylphosphine/palladium(II)acetate, tetrakis-(triphenylphosphine)-palladium, bis(triphenylphosphine)palladium(II)chloride or dichloro[1,1'-bis(diphenylphosphino)-ferrocene]palladium (II), particularly tetrakis-(triphenylphosphine)-palladium or bis(triphenylphosphine)palladium(II)chloride, in the presence of a base, such as aqueous or non-aqueous potassium phosphate, sodium or potassium carbonate, particularly aqueous sodium carbonate, in an inert atmosphere such as argon or nitrogen, in a temperature range preferably between RT and reflux, particularly between RT and 130° C.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

The present invention also relates to the use of a compound according to formula (I) as described herein for the treatment or prophylaxis of chronic kidney disease, congestive heart failure, hypertension, primary aldosteronism and Cushing syndrome.

The present invention also relates to the use of a compound according to formula (I) as described herein for the treatment or prophylaxis of chronic kidney disease.

The present invention also relates to the use of a compound according to formula (I) as described herein for the treatment or prophylaxis of congestive heart failure.

The present invention also relates to the use of a compound according to formula (I) as described herein for the treatment or prophylaxis of hypertension.

The present invention also relates to the use of a compound according to formula (I) as described herein for the treatment or prophylaxis of primary aldosteronism.

A particular embodiment of the present invention is a compound according to formula (I) as described herein for the treatment or prophylaxis of chronic kidney disease, congestive heart failure, hypertension, primary aldosteronism and Cushing syndrome.

Also a particular embodiment of the present invention is a compound according to formula (I) as described herein for the treatment or prophylaxis of chronic kidney disease.

Also a particular embodiment of the present invention is a compound according to formula (I) as described herein for the treatment or prophylaxis of congestive heart failure.

Also a particular embodiment of the present invention is a compound according to formula (I) as described herein for the treatment or prophylaxis of hypertension.

Also a particular embodiment of the present invention is a compound according to formula (I) as described herein for the treatment or prophylaxis of primary aldosteronism.

The present invention also relates to the use of a compound according to formula (I) as described herein for the preparation of a medicament for the treatment or prophylaxis of chronic kidney disease, congestive heart failure, hypertension, primary aldosteronism and Cushing syndrome.

Also an embodiment of the present invention is the use of a compound according to formula (I) as described herein for the preparation of a medicament for the treatment or prophylaxis of chronic kidney disease.

Also an embodiment of the present invention is the use of a compound according to formula (I) as described herein for the preparation of a medicament for the treatment or prophylaxis of congestive heart failure.

Also an embodiment of the present invention is the use of a compound according to formula (I) as described herein for the preparation of a medicament for the treatment or prophylaxis of hypertension.

Also an embodiment of the present invention is the use of a compound according to formula (I) as described herein for the preparation of a medicament for the treatment or prophylaxis of primary aldosteronism.

Also an object of the invention is a method for the treatment or prophylaxis of chronic kidney disease, congestive heart failure, hypertension, primary aldosteronism and Cushing syndrome, which method comprises administering an effective amount of a compound according to formula (I) as described herein.

Also an embodiment of the present invention is a method for the treatment or prophylaxis of chronic kidney disease, which method comprises administering an effective amount of a compound according to formula (I) as described herein.

Also an embodiment of the present invention is a method for the treatment or prophylaxis of congestive heart failure, which method comprises administering an effective amount of a compound according to formula (I) as described herein.

Also an embodiment of the present invention is a method for the treatment or prophylaxis of hypertension, which method comprises administering an effective amount of a compound according to formula (I) as described herein.

Also an embodiment of the present invention is a method for the treatment or prophylaxis of primary aldosteronism, which method comprises administering an effective amount of a compound according to formula (I) as described herein.

Another embodiment of the present invention are compounds of formula (I) as described herein, when manufactured according to any one of the described processes.

Assay Procedures

Herein we identified the use of the G-402 cell line as a host cell to ectopically express (transiently or stably) enzymes of the CYP11 family. Specifically we developed stable G-402 cells expressing ectopically human CYP11B1, human CYP11B2, human CYP11A1, cynmolgus CYP11B1 or cynomolgus CYP11B2 enzyme activity. Importantly the identified cell line G-402 expresses co-factors (adrenodoxin and adrenodoxin reductase) important for the activity of the CYP11 family and no relevant enzyme activity of the CYP11 family (in comparison to H295R cells) was detected in these cells. Therefore the G-402 cell line is uniquely suited as a host cell for the ectopic expression of enzymes from the CYP11 family.

G-402 cells can be obtained from ATCC (CRL-1440) and were originally derived from a renal leiomyoblastoma.

The expression plasmids contains the ORF for either human/cyno CYP11B1 or CYP11B2 under the control of a suitable promoter (CMV-promoter) and a suitable resistance marker (neomycin). Using standard techniques the expression plasmid is transfected into G-402 cells and these cells are then selected for expressing the given resistance markers. Individual cell-clones are then selected and assessed for displaying the desired enzymatic activity using 11-Deoxycorticosterone (Cyp11B2) or 11-Deoxycortisol (Cyp11B1) as a substrate.

G-402 cells expressing CYP11 constructs were established as described above and maintained in McCoy's 5a Medium Modified, ATCC Catalog No. 30-2007 containing 10% FCS and 400 µg/ml G418 (Geneticin) at 37° C. under an atmosphere of 5% CO2/95% air.

Cellular enzyme assays were performed in DMEM/F12 medium containing 2.5% charcoal treated FCS and appropriate concentration of substrate (0.3-10 uM 11-Deoxycorticosterone, 11-Deoxycortisol or Corticosterone). For assaying enzymatic activity, cells were plated onto 96 well plates and incubated for 16 h. An aliquot of the supernatant is then transferred and analyzed for the concentration of the expected product (Aldosterone for CYP11B2; Cortisol for CYP11B1). The concentrations of these steroids can be determined using HTRF assays from CisBio analyzing either Aldosterone or Cortisol.

Inhibition of the release of produced steroids can be used as a measure of the respective enzyme inhibition by test compounds added during the cellular enzyme assay. The dose dependent inhibition of enzymatic activity by a compound is calculated by means of plotting added inhibitor concentrations (x-axes) vs. measured steroid/product level (y-axes). The inhibition is then calculated by fitting the following 4-parameter sigmoidal function (Morgan-Mercer-Flodin (MMF) model) to the raw data points using the least squares method:

$$y = \frac{AB + Cx^D}{B + x^D}$$

wherein, A is the maximum y value, B is the EC50 factor determined using XLFit, C is the minimum y value and D is the slope value.

The maximum value A corresponds to the amount of steroid produced in the absence of an inhibitor, the value C corresponds to the amount of steroid detected when the enzyme is fully inhibited.

EC50 values for compounds claimed herein were tested with the G402-based assay system described. Cyp11B2 enzyme activity was tested in presence of 1 µM Deoxycorticosterone and variable amounts of inhibitors; Cyp11B1 enzyme activity was tested in presence of 1 µM Deoxycortisol and variable amounts of inhibitors.

| Example | EC50 human CYP11B2 µM | EC50 human CYP11B1 µM |
|---|---|---|
| 1 | 0.0014 | 0.1766 |
| 2 | 0.0185 | 0.9355 |
| 3 | 0.0036 | 0.2755 |
| 4 | 0.0293 | 1.2186 |
| 5 | 0.0132 | 1.0824 |
| 6 | 0.0327 | 4.0696 |
| 7 | 0.0088 | 0.82 |
| 8 | 0.027 | 1.0541 |
| 9 | 0.0105 | 0.5156 |
| 10 | 0.029 | 1.2312 |
| 11 | 0.0181 | 0.738 |
| 12 | 0.0074 | 0.2557 |
| 13 | 0.0892 | 5.5679 |
| 14 | 0.0088 | 0.3558 |
| 15 | 0.0196 | 0.6798 |
| 16 | 0.0673 | 2.416 |
| 17 | 0.0022 | 0.3628 |
| 18 | 0.0041 | 0.1716 |
| 19 | 0.0005 | 0.0238 |
| 20 | 0.0116 | 0.5058 |
| 21 | 0.0151 | 0.5693 |
| 22 | 0.0002 | 0.0071 |
| 23 | 0.0125 | 3.1309 |
| 24 | 0.0165 | 2.1413 |
| 25 | 0.0021 | 0.2337 |
| 26 | 0.001 | 0.0448 |
| 27 | 0.001 | 0.0913 |

Compounds of formula (I) and their pharmaceutically acceptable salts or esters thereof as described herein have $EC_{50}$ (CYP11B2) values between 0.000001 uM and 1000 uM, particular compounds have $EC_{50}$ (CYP11B2) values between 0.00005 uM and 500 uM, further particular compounds have $EC_{50}$ (CYP11B2) values between 0.0005 uM and 50 uM, more particular compounds have $EC_{50}$ (CYP11B2) values between 0.0005 uM and 5 uM. These results have been obtained by using the described enzymatic assay.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of aldosterone mediated diseases.

The compounds of formula (I) or their pharmaceutically acceptable salts and esters herein display also variable inhibition of CYP11B1. These compounds may be used for the inhibition of CYP11B1 in combination with variable inhibition of CYP11B2. Such compounds may be used for treatment or prophylaxis of conditions displaying excessive cortisol production/levels or both excessive cortisol and aldosterone levels (for ex. Cushing syndrome, burn trauma patients, depression, post-traumatic stress disorders, chronic stress, corticotrophic adenomas, Morbus Cushing).

In accordance with the invention, the compounds of formula (I) or their pharmaceutically acceptable salts and esters can be used for the treatment or prophylaxis of cardiovascular conditions (including hypertension and heart failure), renal conditions, liver conditions, vascular conditions, inflammatory conditions, pain, retinopathy, neuropathy (such as peripheral neuropathy), insulinopathy, edema, endothelial dysfunction, baroreceptor dysfunction; fibrotic diseases, depression and the like.

Cardiovascular conditions include congestive heart failure, coronary heart disease, arrhythmia, arterial fibrillation, cardiac lesions, decreased ejection fraction, diastolic and systolic heart dysfunction, fibrinoid necrosis of coronary arteries, heart failure, hypertrophic cardiomyopathy, impaired arterial compliance, impaired diastolic filling, ischemia, left ventricular hypertrophy, myocardial and vascular fibrosis, myocardial infarction, myocardial necrotic lesions, myocardial necrotic lesions cardiac arrhythmias, prevention of sudden cardiac death, restenosis, stroke, vascular damage.

Renal conditions include acute and chronic renal failure, end-stage renal disease, decreased creatinine clearance, decreased glomerular filtration rate, diabetic nephropathy, expansion of reticulated mesangial matrix with or without significant hypercellularity, focal thrombosis of glomerular capillaries, global fibrinoid necrosis, glomerulosclerosis, ischemic lesions, malignant nephrosclerosis (such as ischemic retraction, microalbuminuria, nephropathy, proteinuria, reduced renal blood flow, renal arteriopathy, swelling and proliferation of intracapillary (endothelial and mesangial) and/or extracapillary cells (crescents).

Liver conditions include, but are not limited to, liver cirrhosis, liver ascites, hepatic congestion, nonalcoholic steatohepatitis and the like.

Vascular conditions include, but are not limited to, thrombotic vascular disease (such as mural fibrinoid necrosis, extravasation and fragmentation of red blood cells, and luminal and/or mural thrombosis), proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction, and the like.

Inflammatory conditions include, but are not limited to, arthritis (for example, osteoarthritis), inflammatory airways diseases (for example, chronic obstructive pulmonary disease (COPD)), and the like.

Pain includes, but is not limited to, acute pain, chronic pain (for example, arthralgia), and the like.

Edema includes, but is not limited to, peripheral tissue edema, hepatic congestion, splenic congestion, liver ascites, respiratory or lung congestion, and the like.

Insulinopathies include, but are not limited to, insulin resistance, Type I diabetes mellitus, Type II diabetes mellitus, glucose sensitivity, pre-diabetic state, syndrome X, and the like.

Fibrotic diseases include, but are not limited to myocardial and intrarenal fibrosis, renal interstitial fibrosis and liver fibrosis.

Furthermore, the compounds of formula (I) or their pharmaceutically acceptable salts and esters as described herein can also be used for the treatment or prophylaxis of cardiovascular condition selected from the group consisting of hypertension, heart failure (particularly heart failure post myocardial infarction), left ventricular hypertrophy, and stroke.

In another embodiment, the cardiovascular condition is hypertension.

In another embodiment, the cardiovascular condition is heart failure.

In another embodiment, the cardiovascular condition is left ventricular hypertrophy.

In another embodiment, the cardiovascular condition is stroke.

In another embodiment, the compounds of formula (I) or their pharmaceutically acceptable salts and esters can be used for the treatment or prophylaxis renal condition.

In another embodiment, the renal condition is nephropathy.

In another embodiment, the compounds of formula (I) or their pharmaceutically acceptable salts and esters can be used for the treatment or prophylaxis Type II diabetes mellitus In another embodiment, the compounds of formula (I) or their pharmaceutically acceptable salts and esters can be used for the treatment or prophylaxis Type I diabetes mellitus The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

All examples and intermediates were prepared under argon atmosphere if not specified otherwise.

Intermediate A-1

1-Methyl-6-(4,4,5,5-tetramethyl-[1,3,2]dioxaborolan-2-yl)-3,4-dihydro-1H-quinolin-2-one

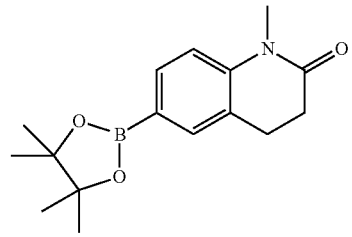 [SMILES: CN1C(=O)CCc2cc(B3OC(C)(C)C(C)(C)O3)ccc21]

[A]
6-Bromo-1-methyl-3,4-dihydro-1H-quinolin-2-one

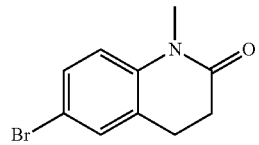

To a solution of 6-bromo-3,4-dihydroquinolin-2(1H)-one (5 g, 22.1 mmol) in DMF (100 mL) cooled to 0° C. was added potassium tert-butoxide (4.96 g, 44.2 mmol) portionwise and the reaction mixture was stirred at 0° C. for 15 min. Then, methyl iodide (4.08 g, 28.8 mmol) was added and the reaction mixture allowed to warm up to room temperature and stirring was continued over night. More MeI (1.25 g, 8.86 mmol) was added and the reaction mixture was heated to 40° C. until completion of the reaction. The mixture was diluted with EtOAc, poured into 100 mL of 1M HCl and the aqueous phase was extracted with EtOAc (2×200 mL). Combined organics were washed with brine, dried over $Na_2SO_4$, filtered and evaporated to dryness. The residue was purified by silica gel flash chromatography eluting with a 0 to 30% EtOAc-heptane gradient to give the title compound (4.23 g, 80%) as an off white solid. MS: 240.0, 242.1 $(M+H^+)$.

[B] 1-Methyl-6-(4,4,5,5-tetramethyl-[1,3,2]dioxaborolan-2-yl)-3,4-dihydro-1H-quinolin-2-one

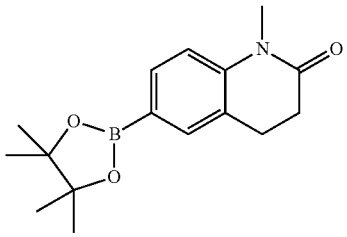 [SMILES: CN1C(=O)CCc2cc(B3OC(C)(C)C(C)(C)O3)ccc21]

A flask was charged with 6-bromo-1-methyl-3,4-dihydro-1H-quinolin-2-one (3 g, 12.5 mmol), 4,4,4',4',5,5,5',5'-octamethyl-2,2'-bi(1,3,2-dioxaborolane) (3.81 g, 15.0 mmol), potassium acetate (3.68 g, 37.5 mmol) and dioxane (48 mL). The mixture was purged with Ar, then dichloro[1,1'-bis(diphenylphosphino)-ferrocene]palladium(II) dichloromethane complex (1:1) [PdCl$_2$(DPPF)-CH$_2$Cl$_2$ adduct] (457 mg, 0.625 mmol) was added and the resulting mixture was heated to 80° C. over night. The reaction mixture was diluted with EtOAc, filtered through Dicalite and washed with EtOAc (2×150 mL). The resulting filtrate was washed with brine, dried over Na$_2$SO$_4$, filtered and evaporated to dryness. The residue was purified by silica gel flash chromatography eluting with a 0 to 40% EtOAc-heptane gradient to give the title compound (2.63 g, 73%) as an off white solid. MS: 288.0 (M+H$^+$).

Intermediate A-2

1-(5-Bromo-pyridin-3-ylmethyl)-6-chloro-1H-pyridin-2-one

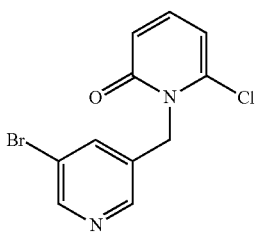 [SMILES: O=c1cccc(Cl)n1Cc1cncc(Br)c1]

[A] 3-Bromo-5-chloromethyl-pyridine

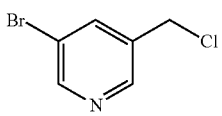

To a solution of (5-bromopyridin-3-yl)methanol (1 g, 5.32 mmol) in DCM (5 mL) was added thionyl chloride (2.53 g, 21.3 mmol) dropwise and the reaction mixture was stirred at room temperature over night. The mixture was diluted with DCM, poured into a 20% aq. NaOH solution (20 mL) and the resulting solution was extracted with DCM (2×25 mL). Combined organics were washed with brine, dried over Na$_2$SO$_4$, filtered and evaporated to dryness to give to the title compound (1.02 g, 93%) as a light brown solid. MS: 208.3 (M+H$^+$).

[B] 2-((5-Bromopyridin-3-yl)methoxy)-6-chloropyridine and 1-(5-bromo-pyridin-3-ylmethyl)-6-chloro-1H-pyridin-2-one

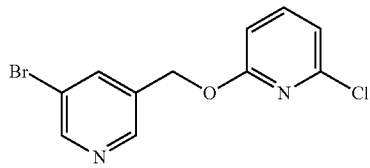

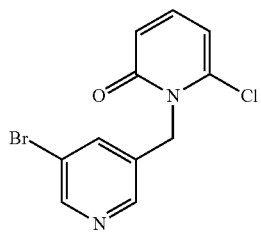

To a solution of 3-bromo-5-chloromethyl-pyridine (0.05 g, 0.242 mmol) in DMF (1 mL) were added 6-chloro-1H-pyridin-2-one (0.031 g, 0.242 mmol) and K$_2$CO$_3$ (0.067 g, 0.484 mmol) and the reaction mixture was stirred at room temperature for 6 h. The mixture was diluted with EtOAc, poured into H$_2$O (3 mL) and the aqueous layer was extracted with EtOAc (2×10 mL). Combined organics were dried over Na$_2$SO$_4$, filtered and evaporated. The residue was purified by silica gel flash chromatography eluting with a 0 to 100% EtOAc-heptane gradient to give 2-((5-bromopyridin-3-yl)methoxy)-6-chloropyridine (0.05 g, 69%) as a colorless liquid, MS: 301.3 (M+H$^+$); and 1-(5-bromo-pyridin-3-ylmethyl)-6-chloro-1H-pyridin-2-one (0.011 g, 15%) as a yellow solid. MS: 301.3 (M+H$^+$).

Intermediate A-3

6-(5-Chloromethyl-pyridin-3-yl)-1-methyl-3,4-dihydro-1H-quinolin-2-one

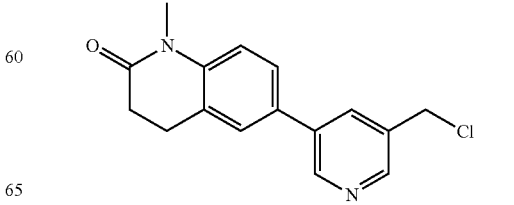

23

[A] 6-(5-Hydroxymethyl-pyridin-3-yl)-1-methyl-3,4-dihydro-1H-quinolin-2-one

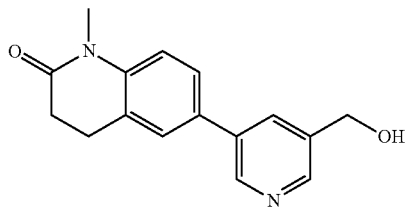 [SMILES: CN1C(=O)CCc2cc(-c3cncc(CO)c3)ccc21]

A sealed tube was charged with (5-bromo-pyridin-3-yl)-methanol (1 g, 5.32 mmol), 1-methyl-6-(4,4,5,5-tetramethyl-[1,3,2]dioxaborolan-2-yl)-3,4-dihydro-1H-quinolin-2-one (intermediate A-1) (1.6 g, 5.58 mmol) and DMF (15 mL). After purging the reaction mixture with argon, bis(triphenylphosphine)palladium(II)chloride (0.373 g, 0.532 mmol) and 1 M aq. $Na_2CO_3$ solution (13.3 mL, 13.3 mmol) were added and the reaction was heated to 120° C. for 1.5 h. The mixture was filtered over Dicalite, washed with EtOAc and the resulting filtrate was evaporated to dryness. The residue was purified by silica gel flash chromatography eluting with a 3 to 10% MeOH-DCM gradient to give the title compound (1.392 g, 97.5%) as a brown solid. MS: 269.5 (M+H$^+$).

24

[B] 6-(5-Chloromethyl-pyridin-3-yl)-1-methyl-3,4-dihydro-1H-quinolin-2-one

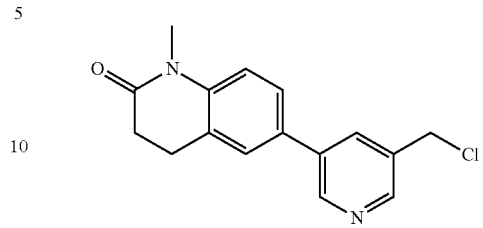

To a solution of 6-(5-hydroxymethyl-pyridin-3-yl)-1-methyl-3,4-dihydro-1H-quinolin-2-one (1.39 g, 5.19 mmol) in DCM (10 mL) was slowly added thionyl chloride (2.47 g, 20.8 mmol) dropwise and the reaction mixture was stirred at room temperature for 3.5 h. The mixture was diluted with DCM, poured into a 20% aq. NaOH solution (20 mL) cooled to 0° C. with an ice bath and the resulting solution was extracted with DCM (2×50 mL). Combined organics were dried over anhydrous $Na_2SO_4$, filtered and evaporated to dryness. The residue was triturated with $Et_2O$, the solid precipitate was filtered off and further dried to give title compound (1.37 g, 90%) as a yellow solid. MS: 287.4 (M+H$^+$).

The following intermediates listed in Table 1 were prepared from 3-bromo-5-chloromethyl-pyridine (intermediate A-2 [A]), in analogy to the procedure described for the preparation of intermediates A-2 [B], using appropriate reaction partners:

TABLE 1

| Intermediate | Name/Structure | Reactant | Aspect | MS (M + H$^+$) |
|---|---|---|---|---|
| A-4 | 3-(5-Bromo-pyridin-3-ylmethyl)-3H-benzothiazol-2-one | 3H-Benzothiazol-2-one | Colorless solid | 323.3 |
| A-5 | 3-(5-Bromo-pyridin-3-ylmethyl)-3H-thiazol-2-one | 3H-Thiazol-2-one | Colorless solid | 271.2 |

TABLE 1-continued

| Intermediate | Name/Structure | Reactant | Aspect | MS (M + H+) |
|---|---|---|---|---|
| A-6 | 1-(5-Bromo-pyridin-3-ylmethyl)-3-chloro-1H-pyridin-2-one | 3-Chloro-1H-pyridin-2-one | Light brown solid | 299.5, 301.3 |
| A-7 | 1-(5-Bromo-pyridin-3-ylmethyl)-3-fluoro-5-trifluoromethyl-1H-pyridin-2-one | 3-Fluoro-5-trifluoromethyl-1H-pyridin-2-one | Light brown solid | 351.3, 353.3 |
| A-8 | 1-(5-Bromo-pyridin-3-ylmethyl)-3-fluoro-1H-pyridin-2-one | 3-Fluoro-1H-pyridin-2-one | Off-white solid | 281.2, 283.3 |

Intermediate A-9

7-Fluoro-1-methyl-6-(4,4,5,5-tetramethyl-[1,3,2]dioxaborolan-2-yl)-3,4-dihydro-1H-quinolin-2-one

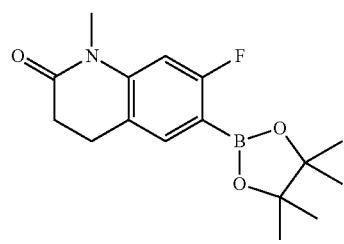 [SMILES: CN1C(=O)CCc2cc(B3OC(C)(C)C(C)(C)O3)c(F)cc21]

[A] 3-Chloro-N-(3-fluoro-phenyl)-propionamide

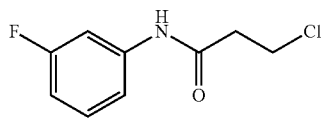 [SMILES: O=C(CCCl)Nc1cccc(F)c1]

To a solution of 3-fluoroaniline (10 mL, 104.02 mmol) in DCM (100 mL) was added pyridine (21 mL, 260.2 mmol) and 3-chloropropionyl chloride (12 mL, 124.4 mmol). The reaction mixture was stirred for 3 hr at room temperature until the starting material had disappeared as shown by LC-MS analysis. The reaction mixture was then diluted with H₂O and extracted with EtOAc. The organic layer was dried over anhy. Na₂SO₄ and concentrated in vacuo to afford the title compound as a solid. It was used in the next step without further purification.

[B] 7-Fluoro-3,4-dihydro-1H-quinolin-2-one

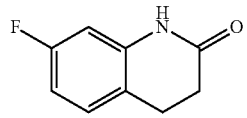

A flame-dried 50-mL flask equipped with a magnetic stirring bar was charged with 3-chloro-N-(3-fluoro-phenyl)-propionamide (10 g, 49.6 mmol) and $AlCl_3$ (23.1 g, 173.6 mmol). On a pre-heated oil bath, the flask was heated at 120~125° C. for 2 hr until a LC-MS analysis indicated the reaction was complete. After cooling to room temperature, the mixture was treated with ice-water slowly. After extraction with EtOAc, the combined organic layers were washed with water and brine in sequence. The organic layer was dried over anhy. $Na_2SO_4$, filtered, and concentrated in vacuo to afford a white solid (7.63 g) as a crude mixture of two regioisomeric products (7-fluoro-3,4-dihydro-1H-quinolin-2-one and 5-fluoro-3,4-dihydro-1H-quinolin-2-one) in a ratio of 5.3:1. This mixture was then refluxed in EtOAc (70 mL) for 30 min before it was cooled to room temperature and concentrated to ~35 mL. The precipitated solid (5.83 g) was collected by vacuum filtration affording the desired 7-fluoro-3,4-dihydro-1H-quinolin-2-one enriched to 95.8%. After repeating three more times the above recrystallization procedure, 4.12 g of the title compound was obtained as a white solid in >99.5% purity.

[C] 7-Fluoro-1-methyl-3,4-dihydro-1H-quinolin-2-one

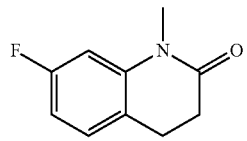

To an ice cold solution of 7-fluoro-3,4-dihydro-1H-quinolin-2-one (16.5 g, 0.1 mol) in DMF (200 mL) was added potassium tert-butoxide (22.4 g, 0.2 mol) in 2 portions. The reaction mixture was stirred at 0° C. for 30 min before MeI (25.4 g, 0.18 mol) was added. After the addition, the reaction mixture was allowed to warm up to room temperature slowly and stirred at room temperature over night. The reaction mixture was diluted with EtOAc (500 mL), then poured into 200 mL of 1 N aq. HCl. After extraction with EtOAc (200 mL, 3×), the combined organic layers were washed with brine, dried over anhy. $Na_2SO_4$, filtered and concentrated in vacuo to give the crude title compound as oil (16.0 g, 89% yield). It was used in the next step without further purification.

[D] 6-Bromo-7-fluoro-1-methyl-3,4-dihydro-1H-quinolin-2-one

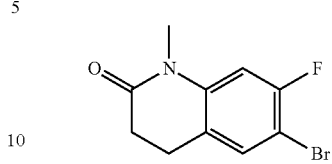

To an ice cold solution of 7-fluoro-1-methyl-3,4-dihydro-1H-quinolin-2-one (16.0 g, 89.4 mmol) in DMF (200 mL) was added NBS (16.0 g, 89.4 mmol). After the addition, the reaction mixture was warmed up to room temperature and stirred for 3 hr. After LC-MS analysis indicated the completion of reaction, the mixture was diluted with EtOAc (500 mL) and poured into water (500 mL). The aqueous layer was then extracted with EtOAc (200 mL, 3×) and the combined organic layers were washed with brine, dried over anhy. $Na_2SO_4$, filtered and concentrated in vacuo to give the crude title compound as oil (18.0 g, 78% yield). It was used in the next step without further purification.

[E] 7-Fluoro-1-methyl-6-(4,4,5,5-tetramethyl-[1,3,2]dioxaborolan-2-yl)-3,4-dihydro-1H-quinolin-2-one

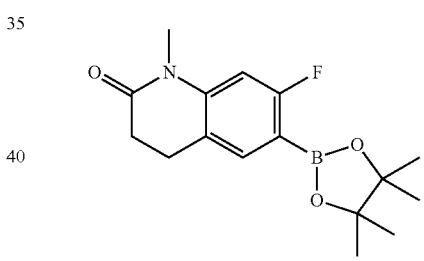

To a mixture of 6-bromo-7-fluoro-1-methyl-3,4-dihydro-1H-quinolin-2-one (18.0 g, 69.8 mmol) in dry dioxane (400 mL) was added 4,4,4',4',5,5,5',5'-octamethyl-2,2'-bi(1,3,2-dioxaborolane) (20.0 g, 83.8 mmol), potassium acetate (20.5 g, 209.4 mmol) and dichloro[1,1'-bis(diphenylphosphino)-ferrocene]palladium(II) dichloromethane complex (1:1) [$PdCl_2$(DPPF)-$CH_2Cl_2$ adduct] (2.55 g, 3.49 mmol). Under argon protection, the reaction mixture was heated at 85° C. over night. After dilution with EtOAc, the mixture was filtered through a Celite pad and the filter cake was washed with additional EtOAc several times. The combined filtrate was then washed with brine, dried over anhy. $Na_2SO_4$, filtered and concentrated in vacuo. Silica gel column chromatography separation (0 to 30% EtOAc in hexane) afforded the crude title compound as white sticky material. Trituration with hexane several times gave the crude product as a light brown solid (10.0 g, 47% yield). MS: 306.1 (M+H$^+$).

Intermediate A-10

6-(5-Chloromethyl-pyridin-3-yl)-7-fluoro-1-methyl-3,4-dihydro-1H-quinolin-2-one

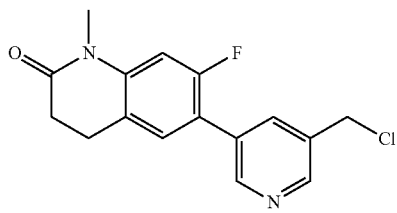 [SMILES: CN1C(=O)CCc2cc(-c3cncc(CCl)c3)c(F)cc21]

In analogy to the procedure described for the preparation of intermediates A-3, (5-bromo-pyridin-3-yl)-methanol has been reacted with 7-fluoro-1-methyl-6-(4,4,5,5-tetramethyl-[1,3,2]dioxaborolan-2-yl)-3,4-dihydro-1H-quinolin-2-one (intermediate A-9) to give 7-fluoro-6-(5-hydroxymethyl-pyridin-3-yl)-1-methyl-3,4-dihydro-1H-quinolin-2-one; further treatment with thionyl chloride then gave the title compound as yellow solid. MS: 305.5 (M+H$^+$).

Intermediate A-11

6-(5-Chloromethyl-4-methyl-pyridin-3-yl)-7-fluoro-1-methyl-3,4-dihydro-1H-quinolin-2-one

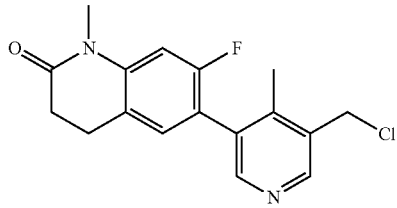 [SMILES: Cc1c(CCl)cncc1-c1cc2c(cc1F)N(C)C(=O)CC2]

In analogy to the procedure described for the preparation of intermediates A-3, (5-bromo-4-methyl-pyridin-3-yl)-methanol has been reacted with 7-fluoro-1-methyl-6-(4,4,5,5-tetramethyl-[1,3,2]dioxaborolan-2-yl)-3,4-dihydro-1H-quinolin-2-one (intermediate A-9) to give 7-fluoro-6-(5-hydroxymethyl-4-methyl-pyridin-3-yl)-1-methyl-3,4-dihydro-1H-quinolin-2-one; further treatment with thionyl chloride then gave the title compound as light brown solid. MS: 319.4 (M+H$^+$).

Example 1

1-Methyl-6-[5-(2-oxo-benzothiazol-3-ylmethyl)-pyridin-3-yl]-3,4-dihydro-1H-quinolin-2-one

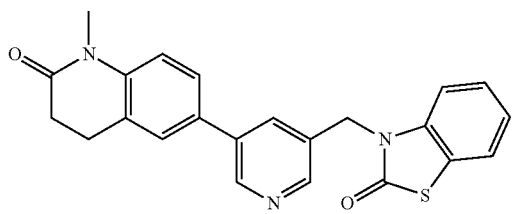 [SMILES: CN1C(=O)CCc2cc(-c3cncc(Cn4c(=O)sc5ccccc54)c3)ccc21]

A sealed tube was charged with 3-(5-bromo-pyridin-3-ylmethyl)-3H-benzothiazol-2-one (intermediate A-4) (0.04 g, 0.125 mmol), 1-methyl-6-(4,4,5,5-tetramethyl-[1,3,2]dioxaborolan-2-yl)-3,4-dihydro-1H-quinolin-2-one (intermediate A-1) (0.039 g, 0.137 mmol) and DMF (1 mL). After purging the reaction mixture with argon, bis(triphenylphosphine)palladium(II)chloride (0.009 g, 0.012 mmol) and 1 M aq. Na$_2$CO$_3$ solution (0.31 mL, 0.31 mmol) were added and the reaction was heated to 100° C. for 1 h. The reaction mixture was diluted with EtOAc, poured into H$_2$O (5 mL) and washed with EtOAc (2×10 mL). The resulting filtrate was washed with brine, dried over anhydrous Na$_2$SO$_4$, filtered and evaporated to dryness. The residue was purified by silica gel flash chromatography, eluting with a 0 to 100% EtOAc-heptane gradient to give the title compound (0.026 g, 52%) as a light red solid. MS: 402.5 (M+H$^+$).

Example 2

6-[5-(5-Fluoro-2-oxo-2H-pyridin-1-ylmethyl)-pyridin-3-yl]-1-methyl-3,4-dihydro-1H-quinolin-2-one

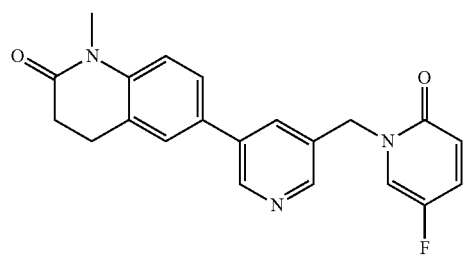 [SMILES: CN1C(=O)CCc2cc(-c3cncc(Cn4cc(F)ccc4=O)c3)ccc21]

To a solution of 6-(5-chloromethyl-pyridin-3-yl)-1-methyl-3,4-dihydro-1H-quinolin-2-one (intermediate A-3 [B]) (0.05 g, 0.147 mmol) in DMF (1 mL) was added 5-fluoro-1H-pyridin-2-one (0.019 g, 0.174 mmol) and K$_2$CO$_3$ (0.048 g, 0.349 mmol) and the reaction mixture was stirred at room temperature over night. The mixture was evaporated to dryness and the residue purified by silica gel flash chromatography eluting with a 0 to 5% MeOH-DCM gradient to give 6-[5-(5-fluoro-pyridin-2-yloxymethyl)-pyridin-3-yl]-1-methyl-3,4-dihydro-1H-quinolin-2-one (0.016 g, 25%), as colorless solid, MS: 364.5 (M+H$^+$); and 6-[5-(5-fluoro-2-oxo-2H-pyridin-1-ylmethyl)-pyridin-3-yl]-1-methyl-3,4-dihydro-1H-quinolin-2-one (0.045 g, 71%) as colorless solid. MS: 364.5 (M+H$^+$).

The following examples listed in Table 2 were prepared in analogy to the procedures described for the preparation of example 1 or example 2 using appropriate starting materials:

TABLE 2

| Ex | Name/Structure | Reactant | Aspect/Reference | MS (M + H$^+$) |
|---|---|---|---|---|
| 3 | 1-Methyl-6-[5-(2-oxo-thiazol-3-ylmethyl)-pyridin-3-yl]-3,4-dihydro-1H-quinolin-2-one | 3-(5-Bromo-pyridin-3-ylmethyl)-3H-thiazol-2-one (intermediate A-5) | Light yellow solid Expl. 1 | 352.4 |
| 4 | 6-[5-(3-Chloro-2-oxo-2H-pyridin-1-ylmethyl)-pyridin-3-yl]-1-methyl-3,4-dihydro-1H-quinolin-2-one | 1-(5-Bromo-pyridin-3-ylmethyl)-3-chloro-1H-pyridin-2-one (intermediate A-6) | Off-white amorphous solid Expl. 1 | 380.5 |
| 5 | 6-[5-(3-Fluoro-2-oxo-5-trifluoromethyl-2H-pyridin-1-ylmethyl)-pyridin-3-yl]-1-methyl-3,4-dihydro-1H-quinolin-2-one | 1-(5-Bromo-pyridin-3-ylmethyl)-3-fluoro-5-trifluoromethyl-1H-pyridin-2-one (intermediate A-7) | Colorless solid Expl. 1 | 432.5 |
| 6 | 6-[5-(3-Fluoro-2-oxo-2H-pyridin-1-ylmethyl)-pyridin-3-yl]-1-methyl-3,4-dihydro-1H-quinolin-2-one | 1-(5-Bromo-pyridin-3-ylmethyl)-3-fluoro-1H-pyridin-2-one (intermediate A-8) | Off-white solid Expl. 1 | 364.5 |

TABLE 2-continued

| Ex | Name/Structure | Reactant | Aspect/ Reference | MS (M + H⁺) |
|---|---|---|---|---|
| 7 | 1-Methyl-6-[5-(6-methyl-2-oxo-2H-pyridin-1-ylmethyl)-pyridin-3-yl]-3,4-dihydro-1H-quinolin-2-one 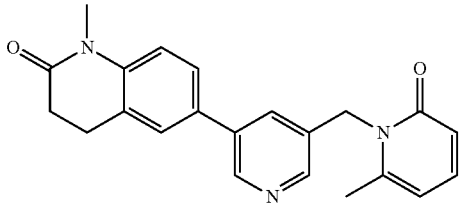 | 6-Methyl-1H-pyridin-2-one | Off-white morphous solid Expl. 2 | 360.5 |
| 8 | 1-Methyl-6-[5-(4-methyl-2-oxo-2H-pyridin-1-ylmethyl)-pyridin-3-yl]-3,4-dihydro-1H-quinolin-2-one 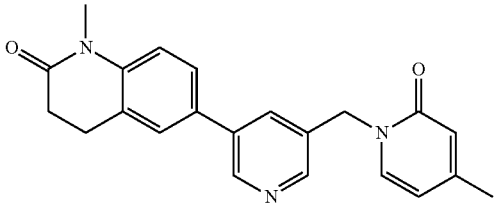 | 4-Methyl-1H-pyridin-2-one | Colorless solid Expl. 2 | 360.5 |
| 9 | 6-[5-(5-Chloro-2-oxo-2H-pyridin-1-ylmethyl)-pyridin-3-yl]-1-methyl-3,4-dihydro-1H-quinolin-2-one 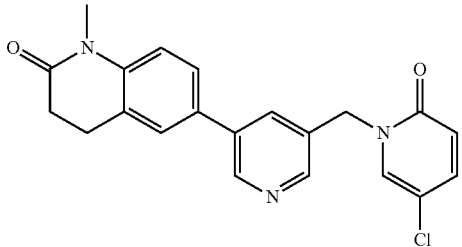 | 5-chloro-1H-pyridin-2-one | Colorless solid Expl. 2 | 380.5 |
| 10 | 1-Methyl-6-[5-(2-oxo-2H-pyridin-1-ylmethyl)-pyridin-3-yl]-3,4-dihydro-1H-quinolin-2-one 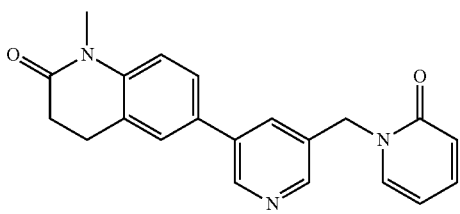 | 1H-Pyridin-2-one | Colorless solid Expl. 2 | 346.5 |

TABLE 2-continued

| Ex | Name/Structure | Reactant | Aspect/Reference | MS (M + H+) |
|---|---|---|---|---|
| 11 | 1-Methyl-6-[5-(2-oxo-3-trifluoromethyl-2H-pyridin-1-ylmethyl)-pyridin-3-yl]-3,4-dihydro-1H-quinolin-2-one | 3-Trifluoromethyl-1H-pyridin-2-one | Colorless solid Expl. 2 | 414.5 |
| 12 | 1-Methyl-6-[5-(2-methyl-6-oxo-6H-pyrimidin-1-ylmethyl)-pyridin-3-yl]-3,4-dihydro-1H-quinolin-2-one | 2-Methyl-3H-pyrimidin-4-one | Colorless amporphous solid Expl. 2 | 361.5 |
| 13 | 1-Methyl-6-[5-(2-oxo-2H-pyrimidin-1-ylmethyl)-pyridin-3-yl]-3,4-dihydro-1H-quinolin-2-one | 1H-Pyrimidin-2-one | Light yellow solid Expl. 2 | 347.6 |
| 14 | 1-[5-(1-Methyl-2-oxo-1,2,3,4-tetrahydro-quinolin-6-yl)-pyridin-3-ylmethy]-2-oxo-1,2-dihydro-pyridine-4-carboxamide | 2-Oxo-1,2-dihydro-pyridine-4-carbonitrile | Colorless solid Expl. 2 | 371.6 |

TABLE 2-continued

| Ex | Name/Structure | Reactant | Aspect/ Reference | MS (M + H+) |
|---|---|---|---|---|
| 15 | 1-Methyl-6-[5-(2-oxo-5-trifluoromethyl-2H-pyridin-1-ylmethyl)-pyridin-3-yl]-3,4-dihydro-1H-quinolin-2-one | 5-Trifluoromethyl-1H-pyridin-2-one | Colorless solid Expl. 2 | 414.6 |
| 16 | 1-[5-(1-Methyl-2-oxo-1,2,3,4-tetrahydro-quinolin-6-yl)-pyridin-3-ylmethyl]-6-oxo-1,6-dihydro-pyridine-3-carbonitrile | 6-Oxo-1,6-dihydro-pyridine-3-carbonitrile | Colorless solid Expl. 2 | 371.6 |
| 17 | 6-[5-(6-Chloro-2-oxo-2H-pyridin-1-ylmethyl)-pyridin-3-yl]-1-methyl-3,4-dihydro-1H-quinolin-2-one | 6-Chloro-1H-pyridin-2-one | Colorless amorphous solid Expl. 2 | 380.5 |
| 18 | 6-[5-(6-Fluoro-2-oxo-2H-pyridin-1-ylmethyl)-pyridin-3-yl]-1-methyl-3,4-dihydro-1H-quinolin-2-one | 6-Fluoro-1H-pyridin-2-one | Colorless amorphous solid Expl. 2 | 364.6 |

The following examples listed in Table 3 were prepared in analogy to the procedure described for the preparation of examples 2, by reacting 6-(5-chloromethyl-pyridin-3-yl)-7-fluoro-1-methyl-3,4-dihydro-1H-quinolin-2-one (intermediate A-10) with the reaction partners listed below:

TABLE 3

| Ex | Name | Reactant | Aspect | MS (M + H⁺) |
|---|---|---|---|---|
| 19 | 7-Fluoro-6-[5-(3-fluoro-2-oxo-2H-pyridin-1-ylmethyl)-pyridin-3-yl]-1-methyl-3,4-dihydro-1H-quinolin-2-one | 3-Fluoro-1H-pyridin-2-one | Colorless solid | 382.6 |
| 20 | 7-Fluoro-1-methyl-6-[5-(4-methyl-2-oxo-2H-pyridin-1-ylmethyl)-pyridin-3-yl]-3,4-dihydro-1H-quinolin-2-one | 4-Methyl-1H-pyridin-2-one | Colorless solid | 378.5 |
| 21 | 6-[5-(5-Chloro-2-oxo-2H-pyridin-1-ylmethyl)-pyridin-3-yl]-7-fluoro-1-methyl-3,4-dihydro-1H-quinolin-2-one | 5-Chloro-1H-pyridin-2-one | Colorless solid | 398.5 |
| 22 | 6-[5-(6-Chloro-2-oxo-2H-pyridin-1-ylmethyl)-pyridin-3-yl]-7-fluoro-1-methyl-3,4-dihydro-1H-quinolin-2-one | 6-Chloro-1H-pyridin-2-one | Colorless solid | 398.5 |

TABLE 3-continued

| Ex | Name | Reactant | Aspect | MS (M + H⁺) |
|----|------|----------|--------|-------------|
| 23 | 7-Fluoro-1-methyl-6-[5-(6-methyl-2-oxo-2H-pyridin-1-ylmethyl)-pyridin-3-yl]-3,4-dihydro-1H-quinolin-2-one | 6-Methyl-1H-pyridin-2-one | Colorless amorphous solid | 378.5 |

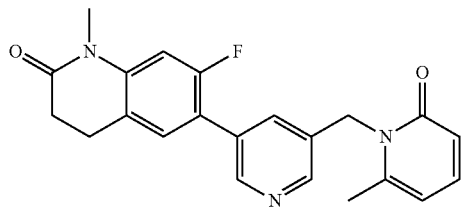

The following examples listed in Table 4 were prepared in analogy to the procedure described for the preparation of examples 2, by reacting 6-(5-chloromethyl-4-methyl-pyridin-3-yl)-7-fluoro-1-methyl-3,4-dihydro-1H-quinolin-2-one (intermediate A-11) with the reaction partners listed below:

TABLE 4

| Ex | Name | Reactant | Aspect | MS (M + H⁺) |
|----|------|----------|--------|-------------|
| 24 | 7-Fluoro-1-methyl-6-[4-methyl-5-(6-methyl-2-oxo-2H-pyridin-1-ylmethyl)-pyridin-3-yl]-3,4-dihydro-1H-quinolin-2-one | 6-Methyl-1H-pyridin-2-one | Light brown amorphous solid | 392.5 |
| 25 | 6-[5-(6-Chloro-2-oxo-2H-pyridin-1-ylmethyl)-4-methyl-pyridin-3-yl]-7-fluoro-1-methyl-3,4-dihydro-1H-quinolin-2-one | 6-Chloro-1H-pyridin-2-one | Light brown amorphous solid | 412.5 |
| 26 | 7-Fluoro-6-[5-(3-fluoro-2-oxo-2H-pyridin-1-ylmethyl)-4-methyl-pyridin-3-yl]-1-methyl-3,4-dihydro-1H-quinolin-2-one | 3-Fluoro-1H-pyridin-2-one | Colorless amorphous solid | 396.5 |

TABLE 4-continued

| Ex | Name | Reactant | Aspect | MS (M + H+) |
|---|---|---|---|---|
| 27 | 7-Fluoro-6-[5-(6-fluoro-2-oxo-2H-pyridin-1-ylmethyl)-4-methyl-pyridin-3-yl]-1-methyl-3,4-dihydro-1H-quinolin-2-one | 6-Fluoro-1H-pyridin-2-one | Light brown amorphous solid | 396.5 |

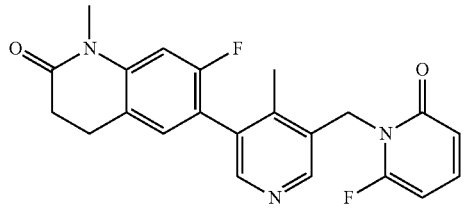

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A Compound of formula (I)

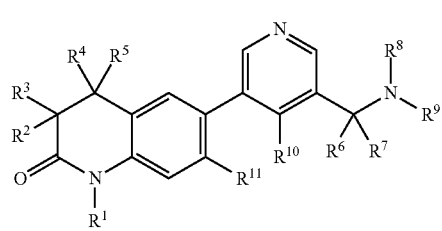

wherein
$R^1$ is H, alkyl, haloalkyl, cycloalkyl or halocycloalkyl;
$R^2$ is H, alkyl, haloalkyl, cycloalkyl or halocycloalkyl;
$R^3$ is H, alkyl, haloalkyl, cycloalkyl or halocycloalkyl;
$R^4$ is H, alkyl, haloalkyl, cycloalkyl or halocycloalkyl;
or $R^3$ and $R^4$ together with the carbon atoms to which they are attached form a double bond;
$R^5$ is H, alkyl, haloalkyl, cycloalkyl or halocycloalkyl;
$R^6$ is H, alkyl, haloalkyl, cycloalkyl or halocycloalkyl;
$R^7$ is H, alkyl, haloalkyl, cycloalkyl or halocycloalkyl;
or $R^6$ and $R^7$ together with the carbon atom to which they are attached form a cycloalkyl;
$R^8$ and $R^9$ together with the nitrogen atom to which they are attached form a heteroaryl substituted with an oxo substituent and one to three substitutents independently selected from H, halogen, cyano, alkyl, haloalkyl, cycloalkyl and halocycloalkyl;
$R^{10}$ is H, halogen, alkyl, haloalkyl, cycloalkyl or halocycloalkyl;
$R^{11}$ is H, halogen, alkyl, haloalkyl, cycloalkyl or halocycloalkyl;
or pharmaceutically acceptable salts or esters.

2. The compound according to claim 1, wherein $R^1$ is alkyl.
3. The compound according to claim 1, wherein $R^2$ is H.
4. The compound according to claim 1, wherein $R^3$ is H.
5. The compound according to claim 1, wherein $R^4$ is H.
6. The compound according to claim 1, wherein $R^5$ is H.
7. The compound according to claim 1, wherein $R^6$ is H.
8. The compound according to claim 1, wherein $R^7$ is H.
9. The compound according to claim 1, wherein $R^8$ and $R^9$ together with the nitrogen atom to which they are attached form a heteroaryl, substituted with an oxo substituent and one to three substitutents independently selected from H, halogen, cyano, alkyl and haloalkyl.
10. The compound according to claim 1, wherein $R^8$ and $R^9$ together with the nitrogen atom to which they are attached form a substituted 2H-pyridinyl, a substituted pyrimidinyl, a substituted thiazolyl or a substituted benzothiazolyl, wherein substituted 2H-pyridinyl, substituted pyrimidinyl, substituted thiazolyl and substituted benzothiazolyl are substituted with an oxo substituent and one to three substitutents independently selected from H, halogen, cyano, alkyl and haloalkyl.
11. The compound according to claim 1, wherein $R^8$ and $R^9$ together with the nitrogen atom to which they are attached form oxo-2H-pyridinyl substituted one to three substitutents independently selected from H, halogen, cyano, alkyl and haloalkyl.

12. The compound according to claim 1, wherein $R^8$ and $R^9$ together with the nitrogen atom to which they are attached form oxo-2H-pyridinyl substituted one to two substitutents independently selected from H, halogen and alkyl.

13. The compound according to claim 1, wherein $R^8$ and $R^9$ together with the nitrogen atom to which they are attached form fluoro-oxo-2H-pyridinyl, chloro-oxo-2H-pyridinyl or methyl-oxo-2H-pyridinyl.

14. The compound according to claim 1, wherein $R^{10}$ is H or alkyl.

15. The compound according to claim 1, wherein $R^{10}$ is alkyl.

16. The compound according to claim 1, wherein $R^{11}$ is H or halogen.

17. The compound according to claim 1, wherein $R^{11}$ is halogen.

18. The compound according to claim 1, selected from
1-Methyl-6-[5-(2-oxo-benzothiazol-3-ylmethyl)-pyridin-3-yl]-3,4-dihydro-1H-quinolin-2-one;
6-[5-(5-Fluoro-2-oxo-2H-pyridin-1-ylmethyl)-pyridin-3-yl]-1-methyl-3,4-dihydro-1H-quinolin-2-one;
1-Methyl-6-[5-(2-oxo-thiazol-3-ylmethyl)-pyridin-3-yl]-3,4-dihydro-1H-quinolin-2-one;
6-[5-(3-Chloro-2-oxo-2H-pyridin-1-ylmethyl)-pyridin-3-yl]-1-methyl-3,4-dihydro-1H-quinolin-2-one;
6-[5-(3-Fluoro-2-oxo-5-trifluoromethyl-2H-pyridin-1-ylmethyl)-pyridin-3-yl]-1-methyl-3,4-dihydro-1H-quinolin-2-one;
6-[5-(3-Fluoro-2-oxo-2H-pyridin-1-ylmethyl)-pyridin-3-yl]-1-methyl-3,4-dihydro-1H-quinolin-2-one;
1-Methyl-6-[5-(6-methyl-2-oxo-2H-pyridin-1-ylmethyl)-pyridin-3-yl]-3,4-dihydro-1H-quinolin-2-one;
1-Methyl-6-[5-(4-methyl-2-oxo-2H-pyridin-1-ylmethyl)-pyridin-3-yl]-3,4-dihydro-1H-quinolin-2-one;
6-[5-(5-Chloro-2-oxo-2H-pyridin-1-ylmethyl)-pyridin-3-yl]-1-methyl-3,4-dihydro-1H-quinolin-2-one;
1-Methyl-6-[5-(2-oxo-2H-pyridin-1-ylmethyl)-pyridin-3-yl]-3,4-dihydro-1H-quinolin-2-one;
1-Methyl-6-[5-(2-oxo-3-trifluoromethyl-2H-pyridin-1-ylmethyl)-pyridin-3-yl]-3,4-dihydro-1H-quinolin-2-one;
1-Methyl-6-[5-(2-methyl-6-oxo-6H-pyrimidin-1-ylmethyl)-pyridin-3-yl]-3,4-dihydro-1H-quinolin-2-one;
1-Methyl-6-[5-(2-oxo-2H-pyrimidin-1-ylmethyl)-pyridin-3-yl]-3,4-dihydro-1H-quinolin-2-one;
1-[5-(1-Methyl-2-oxo-1,2,3,4-tetrahydro-quinolin-6-yl)-pyridin-3-ylmethyl]-2-oxo-1,2-dihydro-pyridine-4-carbonitrile;
1-Methyl-6-[5-(2-oxo-5-trifluoromethyl-2H-pyridin-1-ylmethyl)-pyridin-3-yl]-3,4-dihydro-1H-quinolin-2-one;
1-[5-(1-Methyl-2-oxo-1,2,3,4-tetrahydro-quinolin-6-yl)-pyridin-3-ylmethyl]-6-oxo-1,6-dihydro-pyridine-3-carbonitrile;
6-[5-(6-Chloro-2-oxo-2H-pyridin-1-ylmethyl)-pyridin-3-yl]-1-methyl-3,4-dihydro-1H-quinolin-2-one;
6-[5-(6-Fluoro-2-oxo-2H-pyridin-1-ylmethyl)-pyridin-3-yl]-1-methyl-3,4-dihydro-1H-quinolin-2-one;
7-Fluoro-6-[5-(3-fluoro-2-oxo-2H-pyridin-1-ylmethyl)-pyridin-3-yl]-1-methyl-3,4-dihydro-1H-quinolin-2-one;
7-Fluoro-1-methyl-6-[5-(4-methyl-2-oxo-2H-pyridin-1-ylmethyl)-pyridin-3-yl]-3,4-dihydro-1H-quinolin-2-one;
6-[5-(5-Chloro-2-oxo-2H-pyridin-1-ylmethyl)-pyridin-3-yl]-7-fluoro-1-methyl-3,4-dihydro-1H-quinolin-2-one;
6-[5-(6-Chloro-2-oxo-2H-pyridin-1-ylmethyl)-pyridin-3-yl]-7-fluoro-1-methyl-3,4-dihydro-1H-quinolin-2-one;
7-Fluoro-1-methyl-6-[5-(6-methyl-2-oxo-2H-pyridin-1-ylmethyl)-pyridin-3-yl]-3,4-dihydro-1H-quinolin-2-one;
7-Fluoro-1-methyl-6-[4-methyl-5-(6-methyl-2-oxo-2H-pyridin-1-ylmethyl)-pyridin-3-yl]-3,4-dihydro-1H-quinolin-2-one;
6-[5-(6-Chloro-2-oxo-2H-pyridin-1-ylmethyl)-4-methyl-pyridin-3-yl]-7-fluoro-1-methyl-3,4-dihydro-1H-quinolin-2-one;
7-Fluoro-6-[5-(3-fluoro-2-oxo-2H-pyridin-1-ylmethyl)-4-methyl-pyridin-3-yl]-1-methyl-3,4-dihydro-1H-quinolin-2-one;
7-Fluoro-6-[5-(6-fluoro-2-oxo-2H-pyridin-1-ylmethyl)-4-methyl-pyridin-3-yl]-1-methyl-3,4-dihydro-1H-quinolin-2-one;
and pharmaceutically acceptable salts thereof.

19. The compound according to claim 1, selected from
1-Methyl-6-[5-(2-oxo-benzothiazol-3-ylmethyl)-pyridin-3-yl]-3,4-dihydro-1H-quinolin-2-one;
6-[5-(3-Fluoro-2-oxo-2H-pyridin-1-ylmethyl)-pyridin-3-yl]-1-methyl-3,4-dihydro-1H-quinolin-2-one;
7-Fluoro-1-methyl-6-[5-(6-methyl-2-oxo-2H-pyridin-1-ylmethyl)-pyridin-3-yl]-3,4-dihydro-1H-quinolin-2-one;
7-Fluoro-1-methyl-6-[4-methyl-5-(6-methyl-2-oxo-2H-pyridin-1-ylmethyl)-pyridin-3-yl]-3,4-dihydro-1H-quinolin-2-one;
6-[5-(6-Chloro-2-oxo-2H-pyridin-1-ylmethyl)-4-methyl-pyridin-3-yl]-7-fluoro-1-methyl-3,4-dihydro-1H-quinolin-2-one;
and pharmaceutically acceptable salts thereof.

20. A process to prepare a compound of formula (I) according to claim 1 comprising the reaction of a compound of formula (II) in the presence of a compound of formula (III);

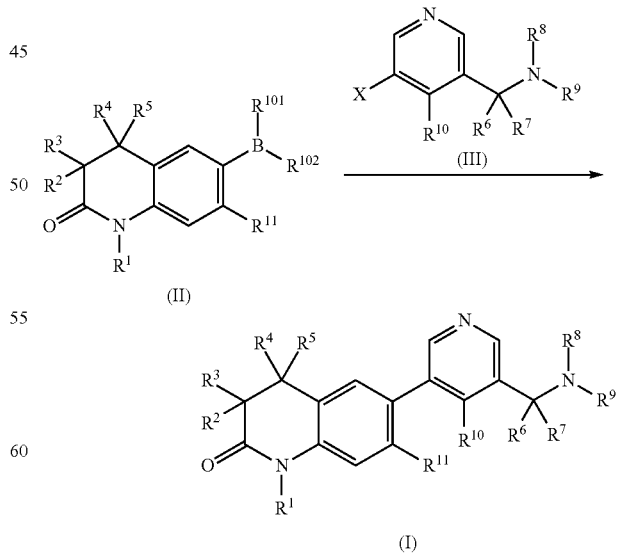

wherein $R^1$, $R^2$, $R^3$, $R^4$, $R^5$, $R^6$, $R^7$, $R^9$, $R^{10}$, $R^{11}$ and A are as defined above, $R^{101}$ and $R^{102}$ are independently selected from alkyl and cycloalkyl, or $R^{101}$ and $R^{102}$ together with the boron atom to which they are attached form a borolane and X is halogen or triflate.

21. A pharmaceutical composition comprising a compound according to claim 1 and a therapeutically inert carrier.

22. The compound of claim 1, when manufactured according to a process of claim 20.

* * * * *